(12) United States Patent
Jornet et al.

(10) Patent No.: US 11,406,266 B2
(45) Date of Patent: Aug. 9, 2022

(54) SMART HEALTHCARE SYSTEM

(71) Applicant: The Research Foundation for the State University of New York, Buffalo, NY (US)

(72) Inventors: Josep Jornet, Clarence Center, NY (US); Liang Feng, Amherst, NY (US); Edward P. Furlani, Lancaster, NY (US); Qiaoqiang Gan, East Amherst, NY (US); Zhi Sun, Clarence Center, NY (US); Yun Wu, East Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 229 days.

(21) Appl. No.: 16/956,465

(22) PCT Filed: Dec. 19, 2018

(86) PCT No.: PCT/US2018/066545
§ 371 (c)(1),
(2) Date: Jun. 19, 2020

(87) PCT Pub. No.: WO2019/126352
PCT Pub. Date: Jun. 27, 2019

(65) Prior Publication Data
US 2021/0121065 A1 Apr. 29, 2021

Related U.S. Application Data

(60) Provisional application No. 62/607,897, filed on Dec. 19, 2017.

(51) Int. Cl.
*A61B 5/1473* (2006.01)
*A61B 5/00* (2006.01)

(52) U.S. Cl.
CPC .......... *A61B 5/0017* (2013.01); *A61B 5/0004* (2013.01); *A61B 5/0022* (2013.01);
(Continued)

(58) Field of Classification Search
CPC ....... A61B 5/00; A61B 5/1473; A61B 5/0031; A61B 5/0017; A61B 5/686; A61B 5/0004;
(Continued)

(56) References Cited

U.S. PATENT DOCUMENTS 8,224,410 B2 * 7/2012 Hadvary ................ A61B 5/411
600/316
10,219,729 B2 * 3/2019 Kintz .................... A61B 5/1459
(Continued)

FOREIGN PATENT DOCUMENTS

WO 03/005890 A2 1/2003

*Primary Examiner* — Eric J Messersmith
(74) *Attorney, Agent, or Firm* — Hodgson Russ LLP

(57) ABSTRACT

A system is provided for advanced health monitoring and diagnosis based on wearable nano-biosensing networks. Nanophotonic and wireless communication technologies are synergistically leveraged to bridge the gap between nano-biosensing technologies and commercial wearable devices. Embodiments of the presently-disclosed system may include: (1) a nanoplasmonic biochip, implanted subcutaneously and built on a flexible substrate; (2) a nanophotonic smart band or wearable device that is able to collect in-vivo signals on-demand and relay them wirelessly to the user's smartphone by means of a secure data transfer; and (3) advanced signal processing techniques implemented on a remote processor to extract relevant data from the received signals and provide a diagnosis in real-time.

16 Claims, 12 Drawing Sheets

(52) U.S. Cl.
CPC .. *A61B 5/14735* (2013.01); *A61B 2562/0285* (2013.01); *A61B 2562/146* (2013.01)

(58) Field of Classification Search
CPC .............. A61B 5/0022; A61B 5/14546; A61B 5/14552; A61B 5/14735; A61B 2562/146; A61B 2562/0285; G01N 21/554; G01N 2201/0221
See application file for complete search history.

(56) References Cited

U.S. PATENT DOCUMENTS

| | | | |
|---|---|---|---|
| 2009/0326344 A1* | 12/2009 | Meyer | G01N 21/77 600/309 |
| 2011/0257494 A1 | 10/2011 | Glazier et al. | |
| 2015/0223738 A1 | 8/2015 | Walavalkar et al. | |
| 2015/0247797 A1* | 9/2015 | Oberg | A61B 5/1451 600/302 |
| 2018/0321150 A1* | 11/2018 | Gavaris | G01N 33/84 |
| 2019/0120763 A1* | 4/2019 | Wu | G06V 40/1324 |
| 2021/0121582 A1* | 4/2021 | Krishnamani | A61B 5/14503 |
| 2021/0162125 A1* | 6/2021 | Altschul | A61B 5/14539 |

\* cited by examiner

SMART HEALTHCARE SYSTEM

CROSS-REFERENCE TO RELATED APPLICATIONS

This application claims priority to U.S. Provisional Application No. 62/607,897, filed on Dec. 19, 2017, the disclosure of which is incorporated herein by reference.

STATEMENT REGARDING FEDERALLY SPONSORED RESEARCH OR DEVELOPMENT

This invention was made with government support under grant no. IIP1718177 awarded by the National Science Foundation. The government has certain rights in the invention.

FIELD OF THE DISCLOSURE

The present disclosure relates to health monitoring systems, and in particular, wearable/implantable systems for health monitoring.

BACKGROUND OF THE DISCLOSURE

In the last few years, the field of wearable devices has increased tremendously—from 28.9 million units shipped in 2014 to 76.1 million units in 2015, a 16% increase in 1 year, and worldwide wearable shipments expected to reach 173.4 million by 2019.

In the last decade, major advancements in the field of micro- and nano-electronics, photonics, electro-mechanical systems and wireless communication technologies have enabled the development of compact wearable devices, with applications in diverse fields such as medical, wellness, sport/fitness, security or even business operations. Importantly, among all the wearable devices that have been released so far, the most popular type were medical devices that collect and transmit health-related data. The interconnection of medical wearable devices in Body Area Networks (BANs) is at the basis of innovative healthcare systems. However, despite their potential, existing wearable devices are only able to measure very few parameters, such as heart rate, breathing, temperature or blood pressure.

In parallel to these efforts, nanotechnology is enabling the development of novel nanosensors that are able to detect different types of events at the nanoscale with unprecedented accuracy. Recently, in-vivo nanosensing systems, which can operate inside the human body in real time, have been proposed as a way to provide faster and more accurate disease diagnosis and treatment than traditional technologies. For the time being, researchers have successfully employed surface plasmon resonance (SPR) sensors to analyze circulating biomarkers in body fluids for the diagnosis of deadly diseases, ranging from different cardiovascular and neuronal diseases to, more recently, different types of cancer directly from blood. Cancer has a huge impact in our society and our economy: in 2015, about 589,430 US residents died of cancer—that is more than 1,600 people a day—and cancer currently accounts for nearly 1 out of every 4 deaths in the United States. However, despite the potential of this technology, there are several limitations in current systems, such as the cost and bulkiness of existing portable systems, which limits the real-world impact of this technology.

BRIEF SUMMARY OF THE DISCLOSURE

A system is provided for advanced health monitoring and diagnosis based on wearable nano-biosensing networks. Nanophotonic and wireless communication technologies are synergistically leveraged to bridge the gap between nano-biosensing technologies and commercial wearable devices. Some embodiments of the presently-disclosed system comprise (1) a nanoplasmonic biochip, implanted subcutaneously and built on a flexible substrate; (2) a nanophotonic smart band or wearable device that is able to collect in-vivo signals on-demand and relay them wirelessly to the user's smartphone by means of a secure data transfer; and (3) advanced signal processing techniques implemented on the smartphone to extract the relevant data from the received signals, and provide a diagnosis in real-time. Moreover, the collected data may be anonymized and stored in a cloud-based database, where it remains accessible to researchers and can be used to develop new understanding and serve as training sets for machine-learning algorithms that can improve automatic diagnosis. The present technology can significantly boost the applications of wearable devices by providing the ability to detect different types of diseases, such as cancer.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
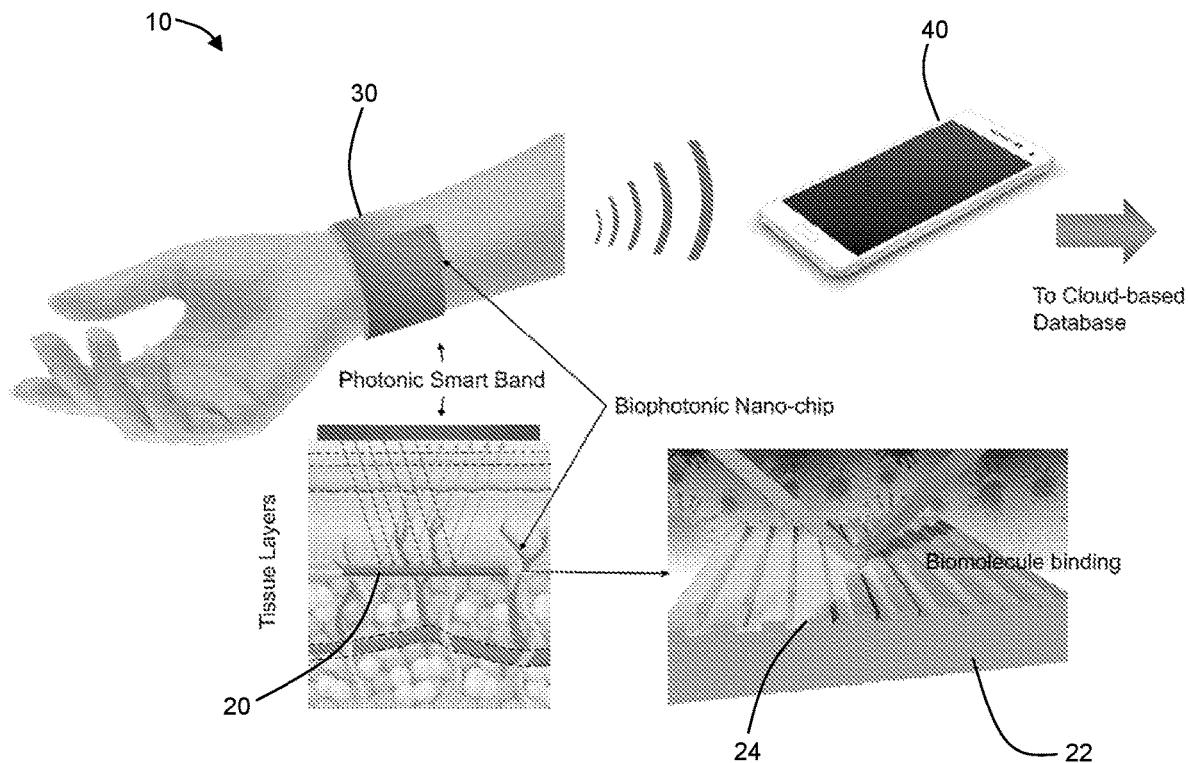
FIG. 1 is a conceptual view of an embodiment of the presently disclosure (sometimes referred to herein as a "WearNet" system)
Figure 2:
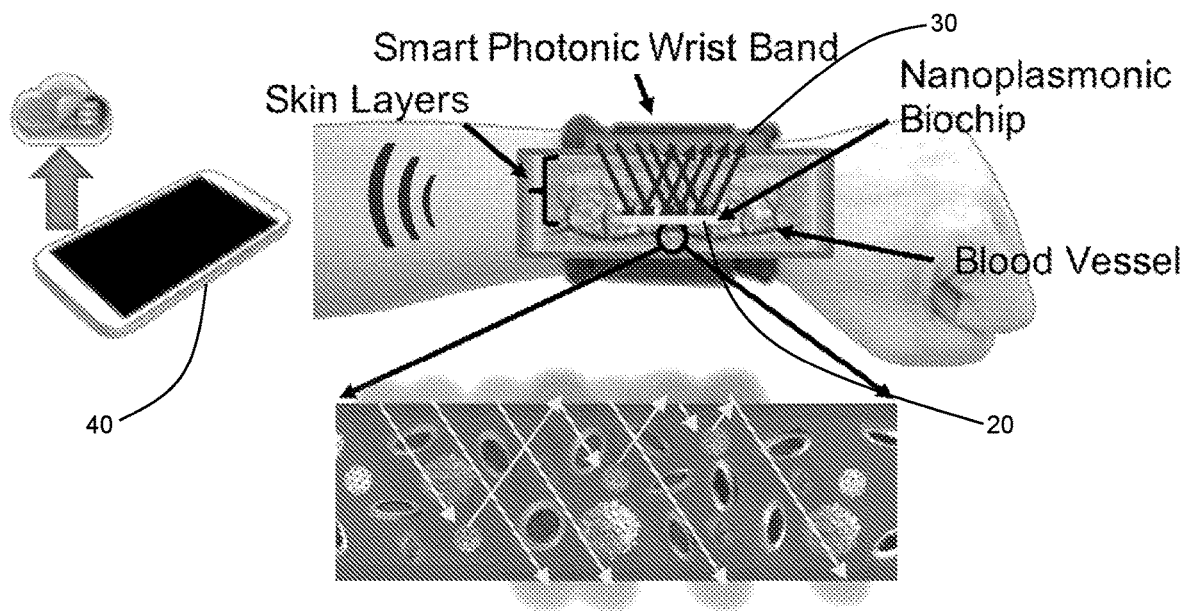
FIG. 2 is a conceptual view of another embodiment of a WearNet system.

In a first aspect, the present disclosure may be embodied as a system 10 (sometimes referred to herein as "WearNet" or the "WearNet system") having an implantable sensor 20 and a wearable interface device 30. (see FIGS. 1-3). The implantable sensor 20 is configured to be implanted subcutaneously in an individual. The implantable sensor 20 may be a nanoplasmonic chip. The sensor 20 comprises an array of surface plasmon resonance (SPR) biosensors 21. For example, the sensor 20 may comprise a thin film 25 made of a material that supports propagation of plasmons—i.e., materials having complex value conductivity (hereinafter called an "SPR film"). More particularly, in some embodiments, the SPR film 25 may be a metallic film such as, for example, gold, silver, or other metals or combinations (alloys) of metals. A plurality of gratings 24 are disposed proximate to the SPR film 25. The plurality of gratings 24 may be made from a dielectric material, such as, for example, silicon. The sensor 20 may be built on a substrate 22, such as, for example, a flexible substrate (e.g., PDMS, etc.) The sensor 20 may include nano-patterns for grating-coupled surface plasmon resonance (SPR)-based detection of the target biomarker. For example, a plurality of gratings 24 may be arranged on a bottom surface of the substrate 22. A target biomarker may be defined by surface-treating the sensor 20 to immobilize selected chemicals. The sensor 20 may further include a plurality of optical couplers 24 located on a top surface of the substrate 22. Each optical coupler 24 is configured such that light received at the optical coupler 24 is focused (i.e., directed) to a corresponding biosensor 21 of the array of SPR biosensors. The sensor 20 is further described below.

The system 10 further includes an interface device 30 configured to be worn by the individual at a location proximate to the implantable sensor 20. The interface device 30 may be, for example, a nanophotonic smart band. The interface device 30 includes a plurality of emitters 32 for emitting excitation energy (for example, light) to the sensor 20. Each emitter 32 of the plurality of emitters is configured to emit light to a corresponding biosensor 21 of the implantable sensor 20. For example, each emitter 32 may emit light which is received by a corresponding optical coupler 24 and directed to a corresponding biosensor 21. The emitted light may be of any appropriate wavelength. For example, the emitted light may be in the visible spectrum, near infrared, far infrared, etc. Each emitter 32 may emit light at the same wavelength as the other emitters or may emit light at a different wavelength from the other emitters. The emitters 32 may be lasers, such as, for example, orbital angular momentum microlasers, single-mode microring lasers, or three-dimensional subwavelength metallo-dielectric semiconductor lasers. The emitters may be the same type of emitters or may be different types of emitters.

The interface device 30 also includes a plurality of detectors 34 for receiving energy (for example, reflected light) from the sensor 20. The plurality of detectors 34 may be, for example, a CCD array. In the example of a CCD array, each pixel of the array, or subsets of pixels of the array, may be considered as a separate detector 34. Each detector 34 is configured to receive light reflected by a corresponding biosensor 21 of the implantable sensor 20.

In this way, active components of the system 10 can be located outside the user's body, and the wearable interface device 30 serves as a nano-to-macro interface between bio-events and the individual.

The system 10 may also include a remote processor 40 for processing data received from the sensor 20 (via the wearable interface device 32, as further described below). The remote processor 40 may be programmed with signal processing algorithms to post-equalize the measured signals by, for example, taking into account the intra-body optical channel, filtering stochastic ambient background noise (created by other biomarkers present in the medium), combining the measured signal at each of photodetector, and, ultimately, providing reliable data to the user or a healthcare practitioner. The collected data may be anonymized and contributed to a cloud-based database, where it can be accessible to researchers both to develop new understanding and as training sets for machine-learning algorithms that can improve automatic diagnosis algorithms.

Contrary to existing portable plasmonic biosensing systems, which rely on a single point of excitation and measurement, the presently-disclosed wearable device may incorporate a network of nano-devices that are able to simultaneously excite and cooperatively reconstruct the response of nanoplasmonic biochips. While the presently-disclosed platform could accommodate different nano-biosensing technologies, the present disclosure will be described with reference to an illustrative, non-limiting embodiment used to monitor the progression of lung cancer. It is noted that the disclosure is not intended to be limited to only this illustrative embodiment, and other applications will be apparent in light of the disclosure. Poor survival of cancer patients is mainly caused by tumor heterogeneity, late diagnosis, lack of effective treatment and cancer recurrence, reflecting the urgent need of next-generation medicine that combines sensitive diagnosis, personalized therapy and effective surveillance to overcome these challenges and improve the survival of cancer patients.

The disclosed system is further described below with respect to four main sections:

Section I is focused on a nanoplasmonic biosensing technology used in some embodiments of the system.

Section II is focused on communication and signal processing, information extraction, and data sharing techniques used in some embodiments of the system.

Section III is focused on the analysis of human factors that may influence embodiments of the system, including, for example, implant regeneration, photothermal effects, and user privacy.

Section IV is focused on an experimental testbed where the nano-biosensing technology and the signal/data processing techniques can be tested in light of the human factors.

I. Plasmonic Nano-Biosensing Technology

In an embodiment, the nanoplasmonic biosensing technology may comprise four main components, namely, (1) an implantable nanoplasmonic biochip having multiplexed sensor arrays, for example, to lung cancer detection from biomarkers in blood; (2) arrayed optical adiabatic couplers for enhancing the light-plasmon coupling efficiency attached to the biochip, the biochip and couplers configured to be embedded underneath the skin of a user; (3) compact optical nano-sources to excite the plasmonic nanoprobes; and (4) arrayed photodetectors able to measure the biosensing signals through reflection, both integrated in a wearable device. See, for example, FIG. 3.

(a) An Implantable Nanoplasmonic Biochip

For convenience and for purposes of illustration, the present system is described herein with reference to the identification of lung cancer. However, the scope of the disclosed system should not be limited to the lung cancer application, and one having skill in the art will recognize that the present disclosure may be broadly applied.

Nanoplasmonic biosensors employing nanoscale topographies are attractive miniaturized platforms for label-free, high throughput and sensitive monitoring of bio/chemical analytes. When receptor molecules are immobilized on nano-structured metal surfaces, the binding of target biomolecules changes the local refractive index (RI), affecting the optical properties of the surface plasmon (SP) modes and permitting optical detection. Recent advances in fabrication, material synthesis, and characterization provide nanoplasmonic sensors with a competitive edge over conventional surface plasmon resonance (SPR) sensors. Most previously-reported plasmonic sensing devices are based on wavelength interrogation. However, high spatial density multiplexed measurements are difficult to achieve in that broadband. Wavelength analysis via spectrometer is required, which inevitably adds to the size and cost of the entire system. A more compact sensing strategy is required to enable in-vivo sensing of biomarkers using an embedded sensing node.

The present device may include a grating-coupled SPR arrangement which is amenable to standard fabrication processes. In an advantageous embodiment, a dielectric coupling grating is on an opposite side of a flat metal film, enabling convenient integration with compact optical couplers (e.g., optical fiber tips) for implantable biomedical sensing.

Figure 5A:
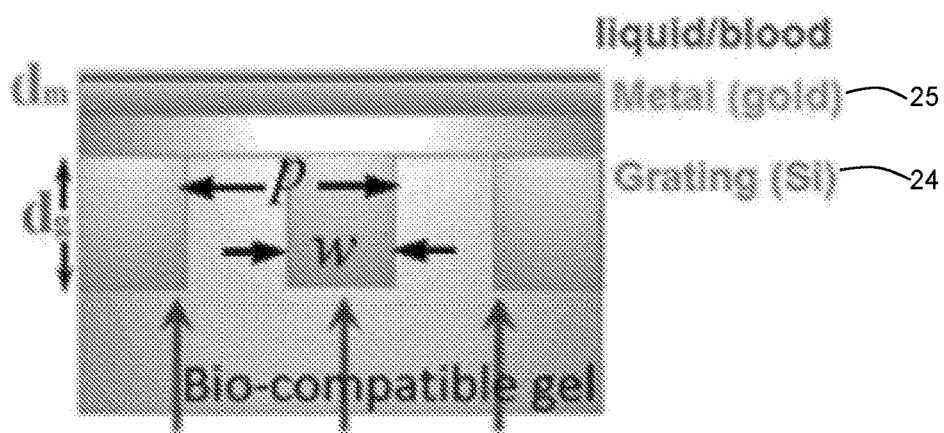
FIG. 5A is a schematic illustration of a dielectric-grating coupling mechanism of the present disclosure from the back side of the metal film.
Figure 5B:
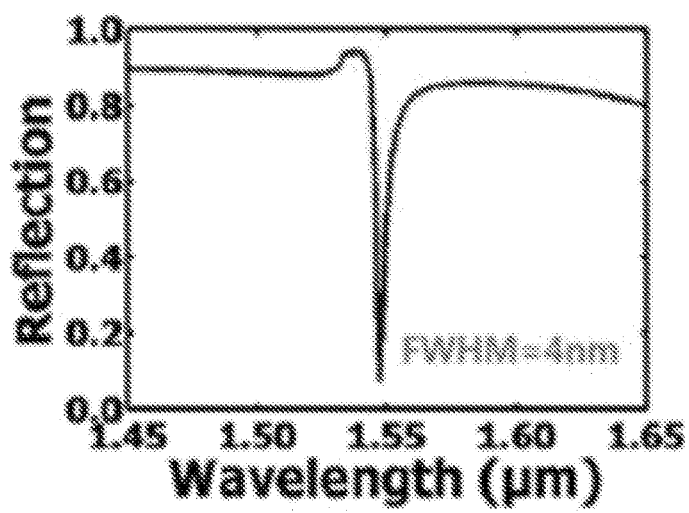
FIG. 5B is a graph showing a modeled reflection spectrum of a grating coupled SPR structure with (p=1150 nm, w=690 nm, $d_g$=300 nm, $d_m$=50 nm)

An example of the structure is illustrated in FIG. 5A. A 50-nm-thick Au film is deposited on a glass substrate followed by a deposition of 350-nm-thick single-crystal Silicon (Si) film. One can then employ standard top-down nanofabrication methods (e.g., optical interference lithography and nanoimprint lithography) to fabricate a grating structure. To further strengthen the adhesion between Au—Si interfaces, titanium or chromium thin-films can be inserted at the Au and Si interface. Transparent biocompatible adhesive materials (e.g., LOCTITE Light Cure Medical Device Adhesives (Henkel Inc.), n≈1.545) can be used to remove (e.g., peel) the layers from the glass substrate, following a recently reported peeling-off procedure. This peeling-off procedure has been used in fabricating large area 1D and 2D metallic nanogratings successfully. In this case, a first side of the metal film is exposed to the environment, which can be used for optical sensing. A second side of the metal film faces the blood to sense circulating biomarkers. With this design, the sensing and detection are located on different sides of the metal film, which will significantly reduce the inference from the blood on the signal collection. By considering the optical constants of the materials (i.e., Si, glass, biocompatible gel, Au, etc.) and setting the period and width of the Si grating to p=1150 nm and w=690 nm, respectively, the reflection spectrum from the Si side under the normal incidence is obtained (FIG. 5B). One can see that an advantageous reflection dip is obtained at the resonant wavelength of 1.547 μm with a very sharp resonance (full width at half maximum (FWHM)=4 nm).

Figure 5C:
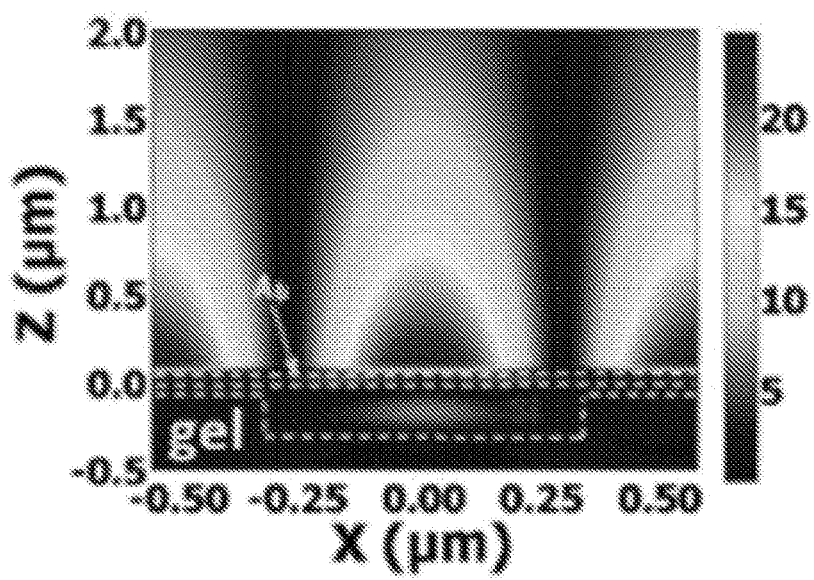
FIG. 5C shows a modeled mode distribution at the resonant wavelength of 1.547 µm.
Figure 5D:
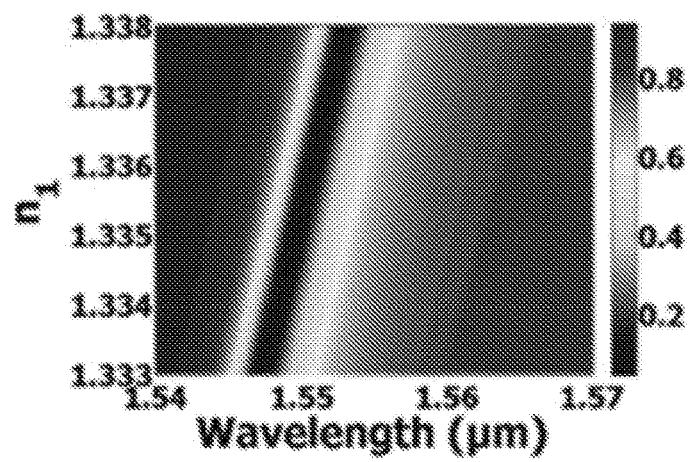
FIG. 5D shows a modeled reflection spectra as the function of the refractive index of the top environment.

To analyze the performance of an exemplary sensor used for testing, the refractive index of the bulk material on the top surface was tuned from 1.333 (i.e., water) to 1.338 and the reflection spectrum was modeled, as shown in FIG. 5D. As the refractive index increases, the resonant wavelength shifts from 1.547 μm to 1.553 μm, demonstrating the spectral sensitivity, $S=\Delta\lambda/\Delta n=1200$ nm/RIU or Refractive Index Units. This number is similar to previously reported wavelength-shift sensitivity for many nanoplasmonic structures reported thus far (e.g., 400 nm/RIU 1500 nm/RIU (λ@1400 1600 nm) for metallic nanopatterns). However, it should be noted that the FWHM of the launched SPP mode is relatively sharp (e.g., only 4 nm in FIG. 5C), resulting in a remarkably high figure-of-merit (FOM=S/FWHM) for spectral sensing. According to the modeled wavelength-shift spectrum shown in FIG. 5D, the estimated FOM is 300, which is much better than reported FOMs obtained by other nanoplasmonic sensor architectures (e.g., typically <10 based on nanoparticles). The best reported FOM records were realized based on double-slit plasmonic interferometer (FOM of ≈200) and nanohole arrays using subradiant dark modes (FOM of 162), respectively, with relatively weak signal-to-noise ratio (SNR) due to the small amplitude of the sensing signal. In contrast, due to the efficient grating coupling mechanism, the amplitude of the SPR resonance is similar to conventional SPR systems with the potential to realize very high SNR and FOM simultaneously. Using a previously reported nanoplasmonic sensor with the FOM of 200, the surface coverage sensitivity was resolved to 0.4 $pg/cm^2$. Therefore, the present metallic nanograting can function as a high performance embedded sensor node with a better surface coverage sensitivity.

Figure 5E:
FIG. 5E is a photograph of a one-time exposed 1D polymer grating structure.
Figure 5F:
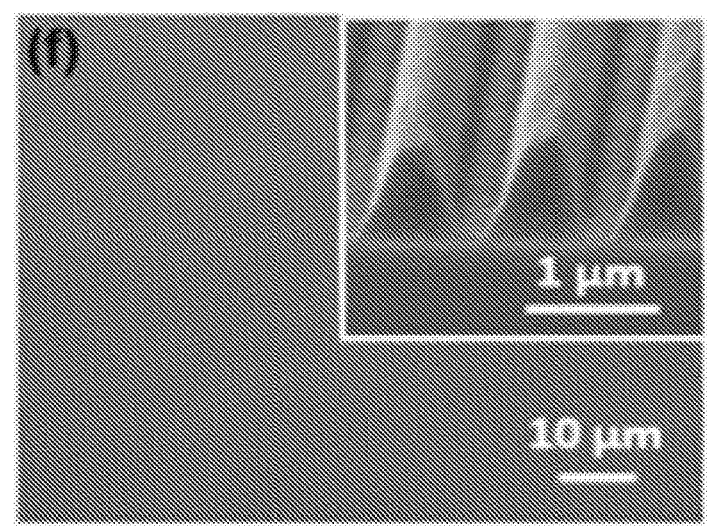
FIG. 5F is a scanning electron microscope ("SEM") image of the one-time exposed 1D polymer grating structure of FIG. 3E (the inset is cross-section SEM image of the 1D polymer grating)

The grating structure may be fabricated using advanced photopatterning processes (e.g., optical interference lithography) over large areas. In recently published work, interference photopatterning technologies were successfully used to fabricate large area polymer holographic gratings and 1D/2D metallic gratings. As shown in FIGS. 5E and 5F, 1D and 2D nanograting patterns were fabricated. In some embodiments of the present system, the optical patterning area could be, for example, 20~30 mm in diameter (FIG. 5E). The exemplary photopatterning process has been scaled up to ~1 meter in diameter for yield production. Note that, while an embodiment of the implantable sensor has a target side length of ~10-100 μm, building large samples and then cutting the sample into small sensors may provide reduced costs. In some embodiments, 2D grating structures are fabricated to address the polarization sensitivity of 1D grating structures. In this case, any polarization direction of the light can be coupled to SP modes efficiently. After that, the gratings on flat metal films may be peeled off using, for example, a bio-compatible gel attached to a glass substrate.

Figure 3:
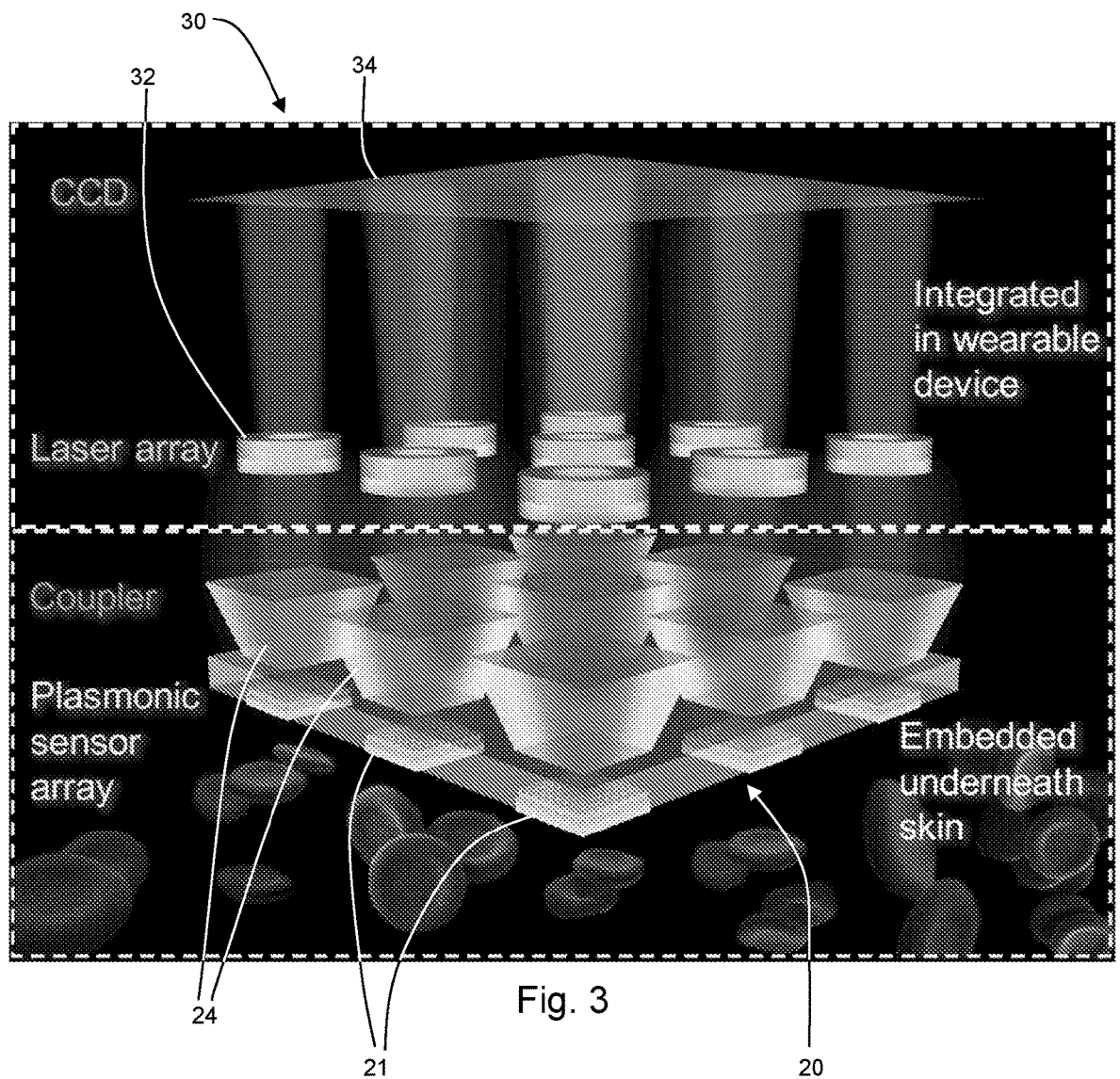
FIG. 3 is a conceptual illustration of an integrated sensor array system according to an embodiment of the present disclosure.
Figure 4A:
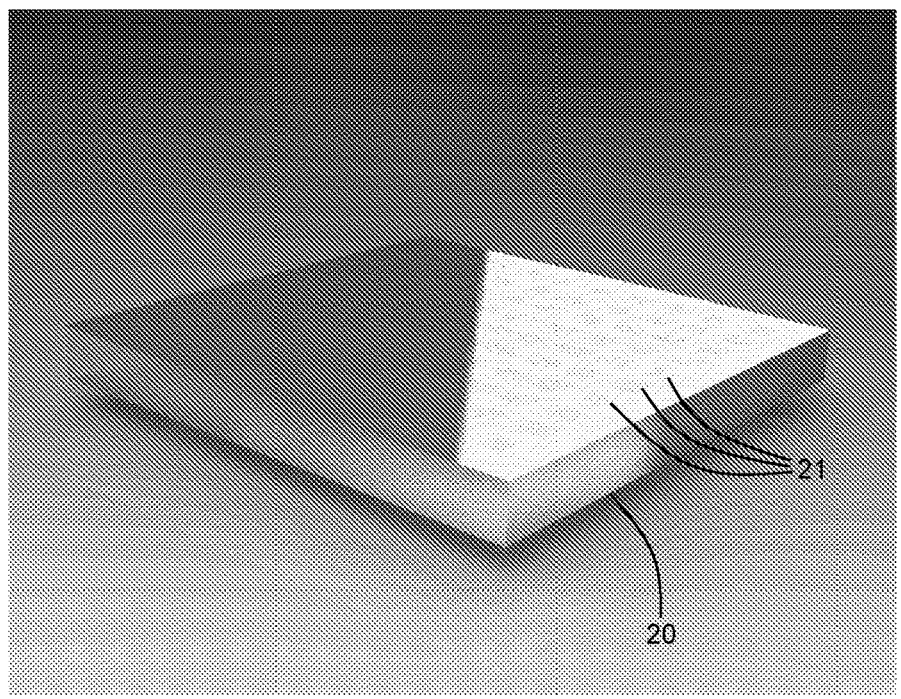
FIG. 4A is an illustration of an exemplary SPR biosensor array according to an embodiment of the present disclosure.
Figure 4B:
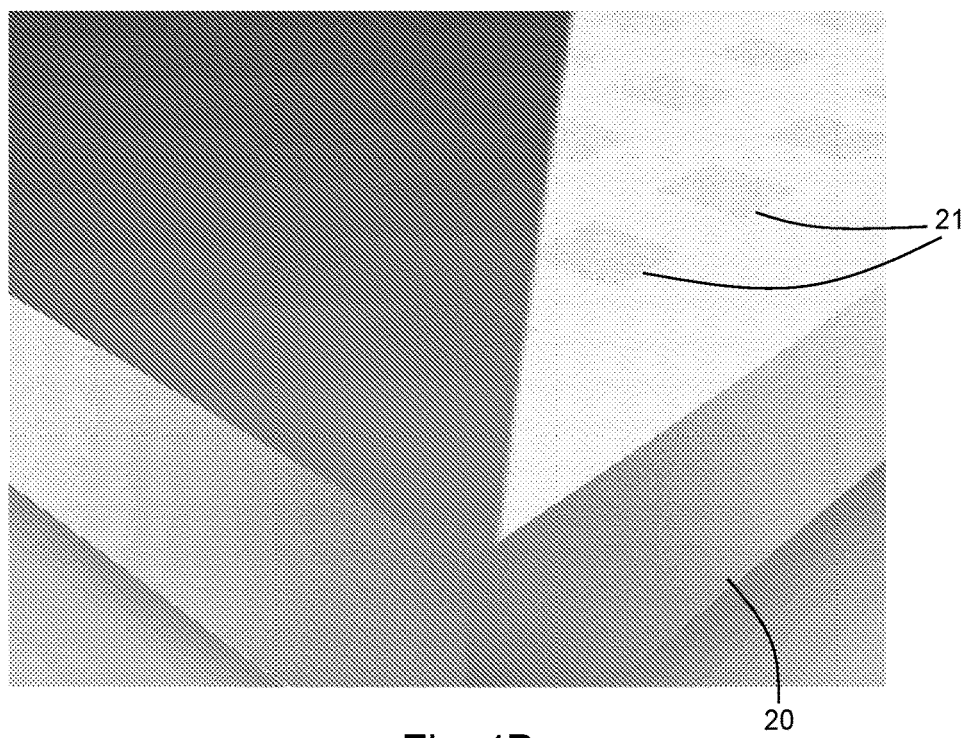
FIG. 4B is a magnified view of a portion of the biosensor array of FIG. 4A.
Figure 4C:
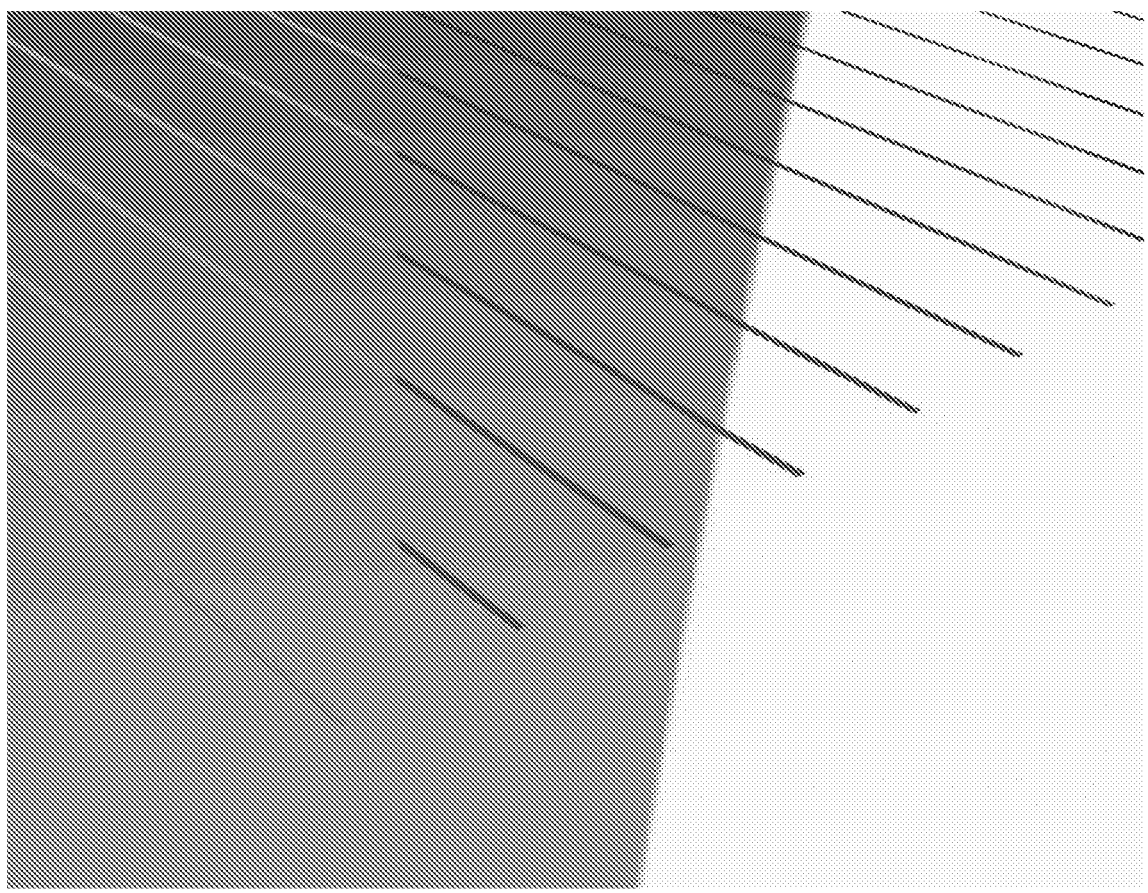
FIG. 4C is a further magnified view of a portion of a biosensor of the biosensor array of FIGS. 4A and 4B.

On the back side of the glass substrate, optical lithography may be employed to identify optical coupler, as illustrated in FIG. 3, which will be used to couple and guide light from the emitter (e.g., ring laser) described in Section I.c as the normal incidence. High-efficiency coupling allows an increase in the depth of the implant within the body. While the target depth for the exemplary embodiment was ~1-2 mm, deeper sites could be reached by increasing the coupler length. Solutions (e.g., water, PBS, etc.) with different refractive indices and standard biomolecules (e.g., BSA, anti-BSA, etc.) may be employed to calibrate the sensing performance of the biochip.

(b) Lung Cancer Biomarker Sensing

In an illustrative embodiment, a nanoplasmonic biochip according the present disclosure may be utilized to monitor circulating CYFRA 21-1 for lung cancer diagnosis and surveillance. Lung cancer was selected as the illustrative disease model because it is the leading cause of cancer deaths worldwide, currently accounting for over 1.37 million deaths a year. The overall five-year survival rate of lung cancer remains 15%, which has not significantly changed since 1970s. In the WearNet platform, the nanoplasmonic biochip may be used to measure the levels of circulating biomarkers in patient blood to, for example: (1) provide information of tumor products in the periphery to complement more invasive and expensive testing; (2) monitor the treatment response to realize personalized therapy; and (3) closely follow the disease progression and predict cancer recurrence.

CYFRA 21-1 is cytokeratin 19 fragment whose levels in the blood are closely related with disease stage, prognosis, and treatment response. High CYFRA 21-1 levels in the blood indicate advanced tumor stage and poor prognosis. Significant decrease of the CYFRA 21-1 level is observed after effective therapy, while insufficient decline of CYFRA 21-1 post treatment indicates poor outcome. Currently, a commercially available CYFRA 21-1 Enzyme Immunoassay (EIA) kit (FUJIREBIO Diagnostics, Inc.) has been approved by U.S. Food and Drug Administration (FDA) to serve as a complementary blood test in monitoring lung cancer progression and evaluating clinical response to therapy. Therefore, CYFRA 21-1 was selected as the model biomarker in the illustrative embodiment used to demonstrate the feasibility of the WearNet system and to compare its sensing performance with the CYFRA 21-1 EIA kit (FUJIREBIO Diagnostics, Inc.)

To detect CYFRA 21-1, the surface of the nanoplasmonic biochip may be coated with a mixture of PEG200 and biotin-PEG1000. Then, biotin-avidin interaction will be used to attach biotinylated monoclonal cytokeratin 19-specific antibody to the surface. In order to achieve the improved sensing performance and reduce non-specific binding, the following parameters were considered: (1) the ratio of PEG200 and Biotin-PEG-1000 (1:1, 1:2, and 1:3); (2) Neutravidin concentration (0.05 and 0.1 mg/mL); (3) antibody concentration (0.05 and 0.1 mg/mL), and (3) the on-chip incubation time of PEG, Neutravidin, and antibody (0.5, 1, and 2 hr). The sensing performance of the exemplary biochip may be evaluated using CYFRA 21-1 antigen spiked in blood samples from healthy controls. The normal range of CYFRA 21-1 in human blood is 0-3.3 ng/ml. Therefore, a serial dilution of CYFRA 21-1 antigen (0-10 ng/mL) may be spiked in blood samples from healthy controls (n=10). The biochip can be used to quantify the concentrations of CYFRA 21-1 antigen based on intensity recovery change (n=6). CYFRA 21-1 EIA kit (FUJIREBIO Diagnositics, Inc.) can also be used to measure the concentrations of CYFRA 21-1 antigen in the same samples. Results can be used to quantify the detection sensitivity and specificity of the biochip and compare with that of CYFRA 21-1 EIA kit.

(c) Design of Optical Excitation Sources

Embodiments of the present device include a plurality of emitters. The emitters may be, for example, an array of optical laser sources to illuminate and excite the nanoplasmonic biochip. The laser sources may be micro/nano optical lasers. For example, an embodiment may include laser resonators based on a III-V semiconductor platform for room temperature lasing action, such as, for example: orbital angular momentum microlasers that directly emit twisted vortex light at the microscale, single-mode microring lasers using parity-time (PT) symmetry, or 3D subwavelength metallo-dielectric semiconductor lasers incorporating a dielectric shield layer. These and/or other laser designs may be used alone or in combination as will be apparent in light of the specification.

Figure 6A:
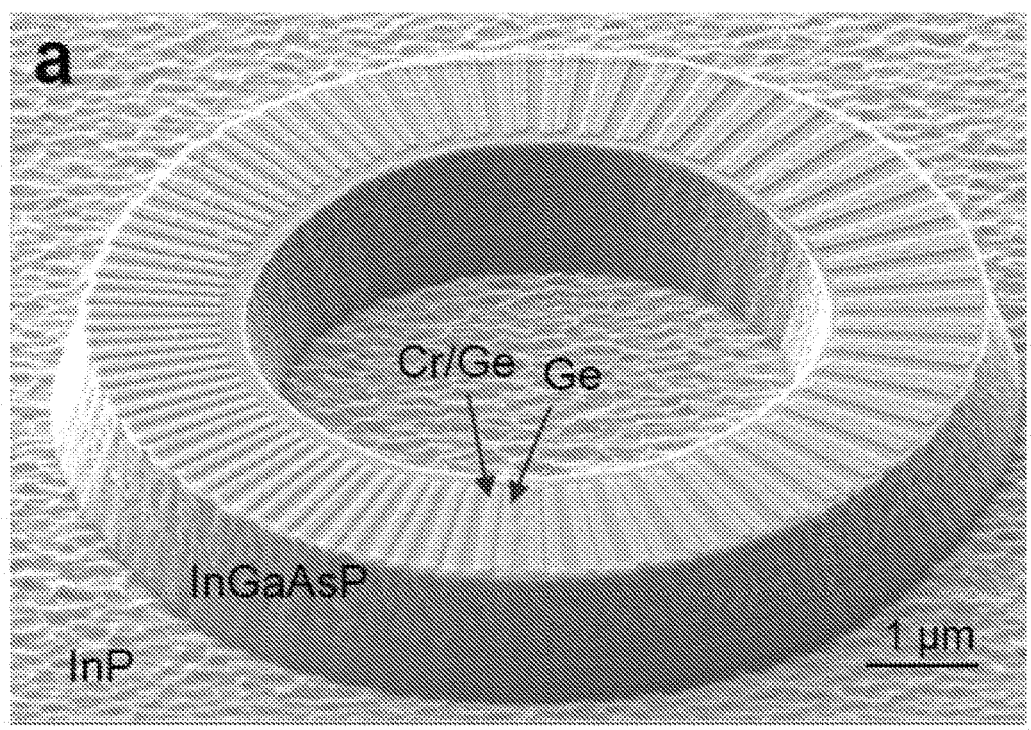
FIG. 6A is an SEM image of a non-Hermitian modulated microring laser fabricated on an InGaAsP/InP platform.
Figure 6B:
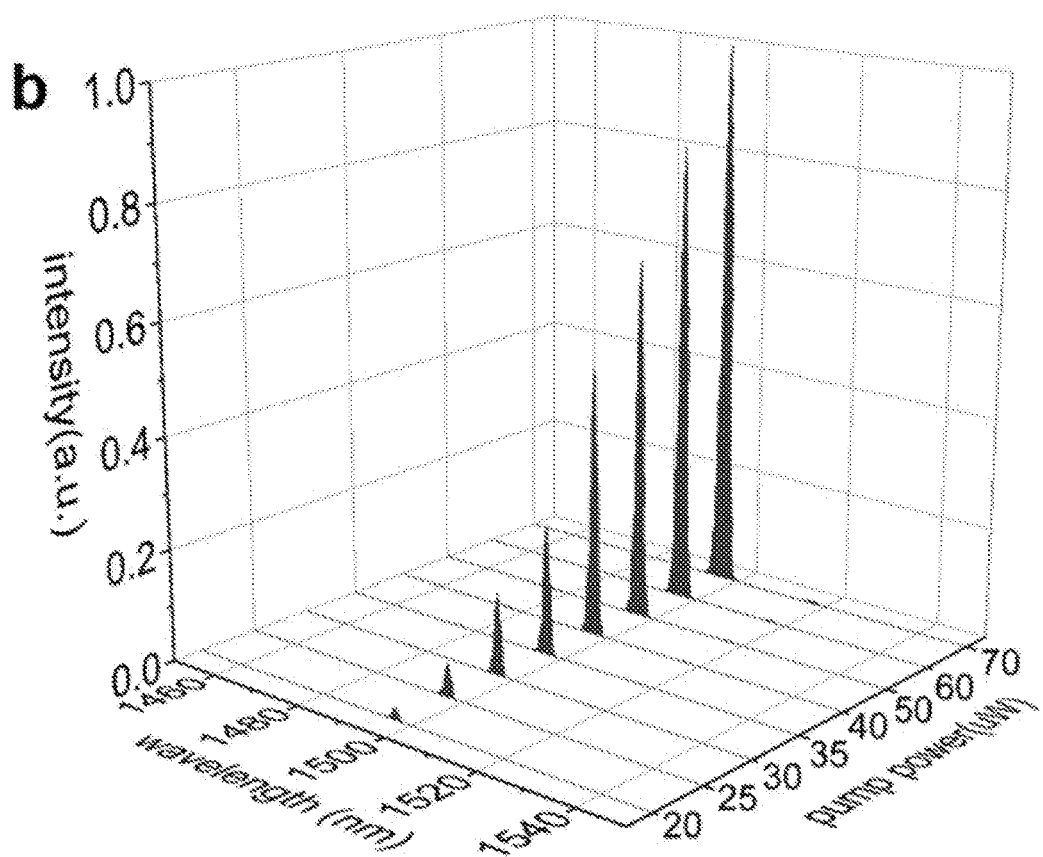
FIG. 6B is a graph showing the emission spectra of the microring laser of FIG. 6A as a function of pump power (the emission spectra clearly show efficient and ultrastable single-mode lasing action at 1500 nm)

In some embodiments, well-developed complementary metal-oxide semiconductor (CMOS) fabrication technologies may be used to fabricate suitable micro/nano lasers on a III-V semiconductor platform, i.e., InP and GaAs composites, according to the laser designs and the conditions from the plasmonic biosensing. In some embodiments, the fabrication of ultrastable micro laser sources may make use of overlay lithography with alignment error controlled below 10 nm. For example, FIG. 6A shows a fabricated complex-index-modulated microring laser cavity using the overlay lithography. The properties of the laser sources may be characterized, for example, as shown in FIG. 6B, where ultrastable single-mode operation was successfully demonstrated with pump power consumed only on the order of μW. It is worth noticing that the preliminary results in FIG. 6B show the laser action in the telecom band around the wavelength of 1500 nm, matching the operational wavelength range of an exemplary nanoplasmonic biochip. Laser characteristics such as, for example, polarization, emission directionality, wavefront shape, and/or wavelength optimization may be tuned so as to further enhance a laser's use in nanoplasmonic biosensing. Thermo-optical modulations may also be used in the integration of the micro/nano laser sources to enable precise control for achieve a desired laser wavelength.

Another advantageous feature of such micro/nano laser sources is their intrinsic ability to be highly distributed. With the emission directionality and power of each individual micro/nano laser precisely controlled, the highly-distributed feature dramatically simplifies the integration of a number of laser sources around the wearable device (e.g., a watch-like form factor, see FIGS. 1 and 2) in the fashion of forming an optical nano-network to specifically enhance the illumination and excitation of the nanoplasmonic biochips. As such, nanophotonic arrays can be integrated and controlled to aid the detection of the received signals in favor of optimized computer algorithms.

(d) Photodetection of Bio-Signals

Once light from the emitters is reflected from the implantable sensor (thus carrying the biosensing signal) the reflected light is detected and measured. In the presently-disclosed wearable device, an array of photo-detectors, such as a charge-coupled device (CCD) camera chip, can be integrated on a different physical layer, for example, above the emitters (optical sources), to capture the reflected light. In an exemplary embodiment, each photo-detector, e.g., each individual pixel on a CCD chip, or subsets of pixels of a CCD chip, can be aligned with each optical source and its corresponding nanoplasmonic bio-pixel to efficiently capture the sensing signal through reflection. Where the emitters are microlasers, the cavities may be ring-shaped, favoring the transmission of reflected light through central hollow area of each emitter to its corresponding detector. Here, it is also noted that while a III-V semiconductor InP chip (in the illustrative embodiment) looks opaque with visible light, it is transparent for other wavelengths, for example, the "telecom" window of around 1500 nm.

Despite using a network of micro/nano sources, the biosensing signals to be measured are expectedly weak, at least when compared to traditional desktop or portable biosensors equipped with large-size lasers, due to the much lower excitation power. To overcome this problem, in some embodiments of the present system, the micro/nano-lasers individually switch on and off to collect spatially distributed data (see further description below Section II).

II. Computing, Sensing and Information Technologies: Nano-Biosensing Body-Area Networks After measuring the response signals from the nanoplasmonic biochip on the distributed detectors embedded at the wearable device, the information is transmitted to the user's smartphone. To provide compatibility with virtually every smartphone in the market, Bluetooth may be utilized for data transfer. It should be noted that other wireless technologies exist and others are under development for BANs. Any of these technologies may be used. The much larger computational power of the smartphone can be leveraged to implement real-time algorithms to aggregate the response signals, eliminate the impacts from multi-path scattering in the intra-body channel, extract the relevant information to generate a diagnose, and securely share the data and diagnose with an online cloud-based database.

(a) Data Reconstruction and Analysis

Figure 7:
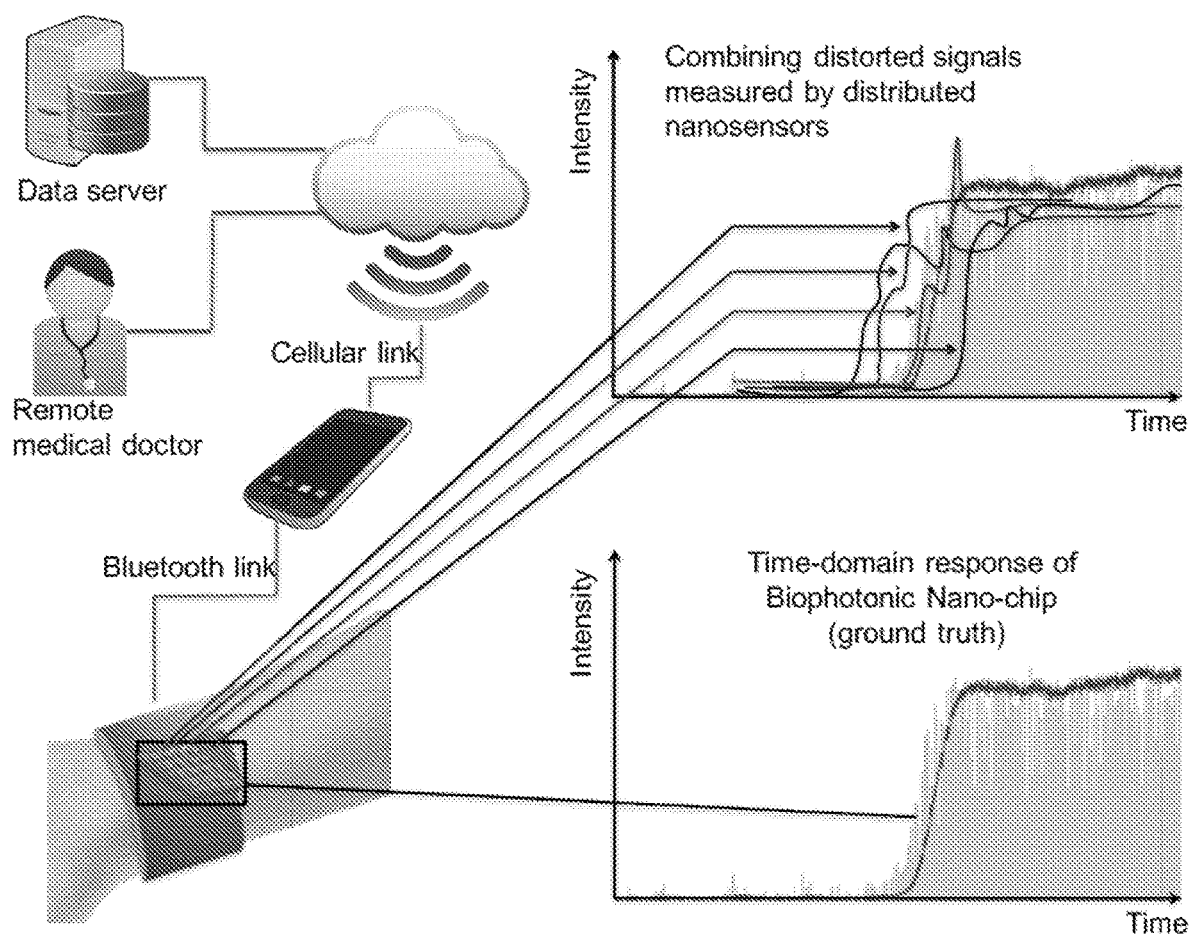
FIG. 7 is a diagram depicting data reconstruction and sharing in an embodiment of a WearNet system.

Data reconstruction and analysis techniques can be used to enhance the useful information to be extracted from the large amount of measurements captured by the plasmonic nano-biosensing network. As illustrated in FIG. 7, the plurality of detectors across the wearable device send their measurements via a transceiver (for example, a Bluetooth transceiver) from the wearable device to the remote processor (for example, a smartphone), where the data reconstruction and analysis are conducted. As discussed in Section I.c, a large number of detectors may be deployed to (i) enhance the measured signal strength and (ii) explore the spatial diversity to improve signal quality.

Data Reconstruction Through Optimal Combining Distributed Measurements

An objective of data reconstruction is to accurately rebuild the time-domain response of the implanted nanoplasmonic biochips using a large number of independent measurements, obtained from the network of detectors on the wearable device.

As discussed above, a large amount of data points may be beneficial for each measurement. These may be obtained from many distributed detectors that are deployed across the wearable device and experience different channel attenuation, signal distortion, and delay. There are three key influential factors that may be considered for data reconstruction: (1) the intra-body channel that affects the propagation of optical signals from the light sources to the biochip and back to the detectors; (2) the nontrivial distortion, noise, and delay introduced when capturing and digitizing the received signals at each detector; and (3) the offsets between the measurements reconstructed at each detector in terms of arrival time, rising time, and amplitude.

Figure 8A:
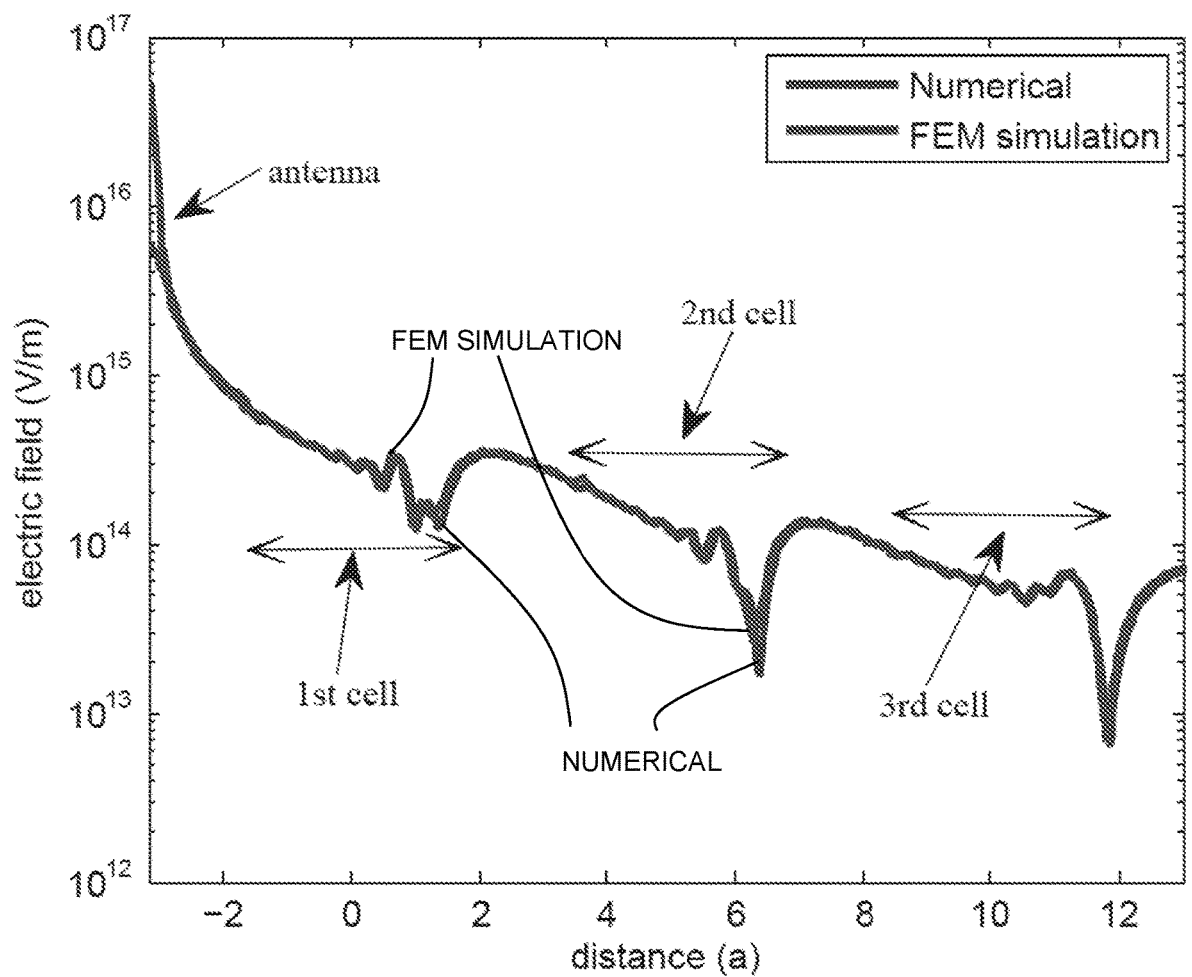
FIG. 8A is a graph showing a path loss of optical signals in intra-body channel.
Figure 8B:
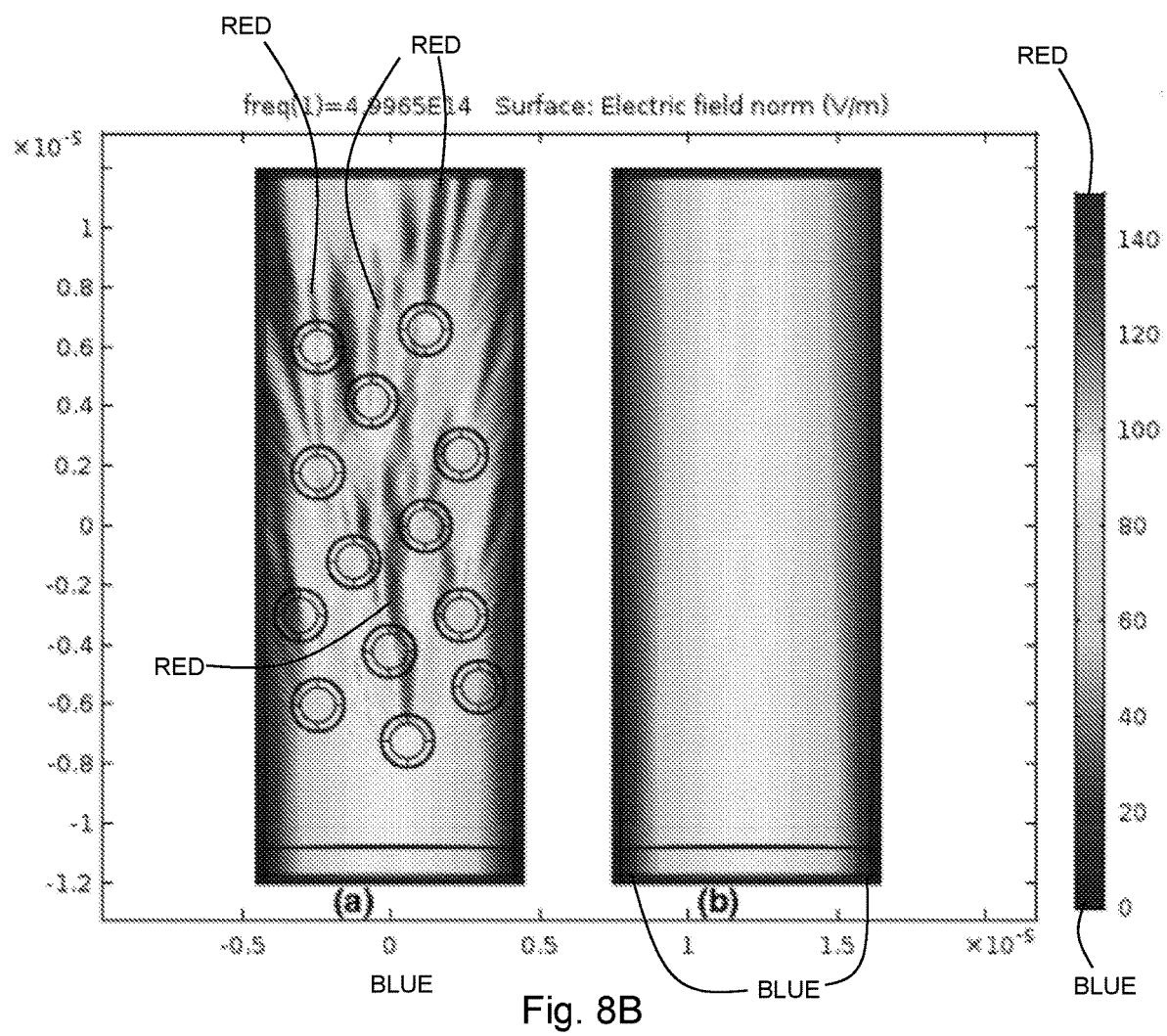
FIG. 8B shows signal scattering in a multi-cell environment (from a previous model)
Figure 8C:
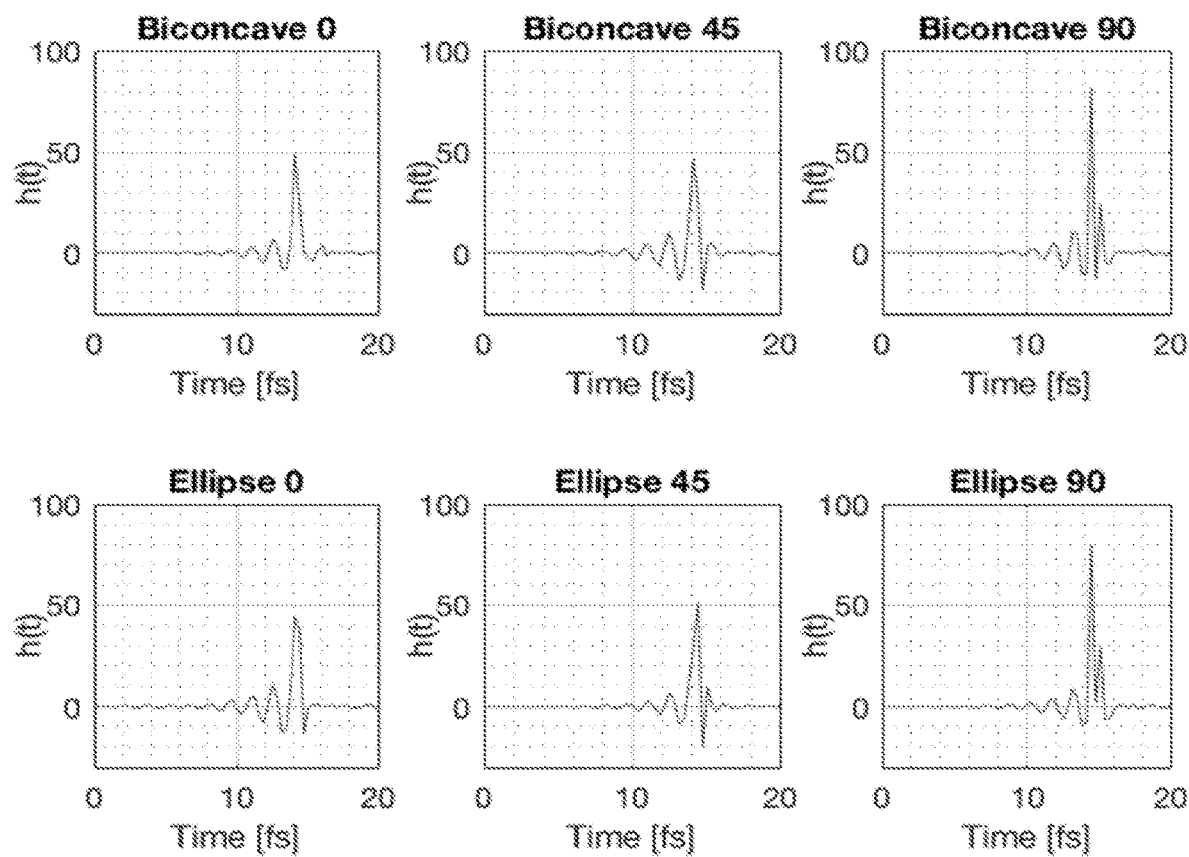
FIG. 8C is a set of graphs showing channel impulse response for different cell shapes (from a previous model)

Channel effects: A novel intra-body channel model has been developed to characterize the signal propagation and distortion between the nanoplasmonic biochip and the detectors through different body components, including blood and other body fluids, vessel walls, bones, muscles, fat and skin. The model is different from traditional channel models where the human body is described as a layered material with different permeability and permittivity, In the present model, the intra-body channel is characterized from the perspective of the detectors: the body is a collection of different types of elements, such as cells, organelles, proteins, and molecules, with different geometry and arrangement as well as different EM properties. Moreover, while existing models are mostly valid only when a large area (in terms of wavelength) is illuminated, a channel model is developed that works when nano-sources with very small apertures are utilized. The present models can accurately predict the channel path loss by taking into account the absorption from different types of molecules and the scattering by different types of cells. In FIG. 8A, the signal path loss is shown as a function of distance under the influence of the cells in the intra-body channel. In FIG. 8B, the significant scattering effects are illustrated when optical waves propagate through a group of cells. In FIG. 8C, the channel impulse response for different shapes of the cells is plotted in time domain, which shows different type, position, and direction of the cells in the intra-body channel can dramatically change the delay and shape of the response signal from the nanoplasmonic biochip. The intra-body channel models can be used to estimate the attenuation, delay, and distortion caused by the signal propagation inside human body. On the one hand, a link-budget analysis can be performed to estimate the required emission power of nano/micro-lasers (Section I.c, with the human factors constraints in Section III.b)), and the number, size and depth of the implants (Sections I.a and I.b with the human factor constraints in Section III.a). On the other hand, by utilizing the developed models, the influence of the intra-body channel can be mitigated by post-equalization.

Signal reconstruction at each detector: The weakened optical signals received at each photodetector can be digitized for signal processing purposes. In the process of converting the captured analog signal to digitized data, additional distortion and noise is introduced. First, any non-linearity of the photodetectors introduces additional distortion. Second, the analog-to-digital converter (ADC) converts the captured continuous analog signal to a digital signal sequence. In real world operation, practical ADCs can bring quantization error and integral nonlinearity (INL), which can further distort the reconstructed signal at each detector. These factors can be analyzed, and the reconstructed signals can be corrected accordingly.

Data reconstruction at a remote processor (for example, a mobile device such as a smartphone): Although a Bluetooth wireless link can transmit a digitized signal captured by each detector to a smartphone, it is still challenging to accurately reconstruct the response signal from the large number of distributed nanosensors. An example of data reconstruction in a WearNet system is illustrated in FIG. 7. As shown in the figure, the relevant diagnosis information of the ideal (ground truth) response signal from the nanoplasmonic biochip lies in the transient part of the time-domain signal. Since the signal transient may be very short and very sensitive to noise, delay, and distortion, an objective of the data reconstruction algorithm in WearNet may be to control and mitigate those impacts. In order to overcome self-reflectance and noise, the arrayed nanolasers may be individually controlled and space sweeping algorithms can be used to first localize the nanosensor and then focus on the actual device and collect the data (Section I.c). Since different detectors may be placed at different locations in the wearable device, the measured signals experience different channel influences during the propagation inside human body. In addition, in some embodiments, a photodetector and an ADC at each detector can impose unique distortions to each reported digitized signal. Moreover, the time spot of each measurement can be slightly different from each other since there is no strict synchronization among the detectors.

In light of all these phenomena, the remote processor may be programmed to combine the large number of measurements with significant offsets from the detectors. First, together with the efforts that mitigate the influence from the intra-body channel and hardware of the detectors, the offsets caused by the channel and sensor hardware may be reduced. Second, the spatial and temporal correlations among the detectors may be used to further reduce the offsets, by running calibration algorithms that exploit the capability of switching on/off individual micro/nano-lasers (the locations of the detectors are supposed to be known through the communication between the wearable devices and the smartphone).

Information-theoretic Data Analysis: The digital data reconstructed at the remote processor provides the raw materials for smart health diagnosis. Compared with the traditional wearable devices that take simple heart rate or blood glucose (can be considered as a 1-digit data), the presently-disclosed detectors network system can provide tremendously detailed information for automatic or remote health diagnosis. The reconstructed response signal from the nanoplasmonic biochip may be analyzed from an information-theoretic perspective to extract useful information for diagnosis.

Information capacity of reconstructed biochip response signals: The amount of information which can be delivered by the presently-disclosed wearable nano-biosensing networks can be characterized. In particular, the amount of information carried by the reconstructed response signal from the nanoplasmonic biochip can be characterized (the "information" is the mutual information, i.e., how much uncertainty (entropy) of the diagnosis of a certain disease, e.g., lung cancer, can be reduced by analyzing the reconstructed response signal). The impact of the intra-body channel, detectors hardware, and the offset among distributed measurements can be quantitatively captured so that improved strategies can be determined according to the resulted information capacity.

Useful information extraction from reconstructed biochip response signals: Although the information capacity of biochip response signals can be extremely large, not every single bit of the capacity may be essential for the disease diagnosis. Where present, such non-essential information in the reconstructed response signal from the nanoplasmonic biochip may create unnecessary requirements for hardware precision and computation complexity. Moreover, the non-essential information also increases the diagnosis complexity. To this end, a data extraction process may be used to derive the essential diagnosis information from the biochip temporal signals. Such a data reduction process may use dimensionality reduction techniques, such as PCA and Fisher LDA, to find the most discriminant subspaces of signals that can highlight the relevant features of the monitored biological process. A dimensionality reduction solution may rely on the database of diagnosis results that are based on the response signal from the biochip.

(b) Data Sharing and System Self-Learning

The system may also provide for data sharing and/or database. The system may include data sharing for WearNet system so that the health monitoring information from users and diagnosis results can be used for system learning. In this way, automatic diagnosis may be used. The WearNet system may provide, for example, data regarding the measured time-response of the biochip. Such data may need to be interpreted by a medical doctor to generate a diagnostic. Ultimately, the measured responses and the doctor's diagnoses may be used to generate and train new algorithms for accurate one-to-one matching and diagnostics. For example, the learning mechanism may be formulated as a classification problem: the extracted information from the WearNet is used as the input feature and the diagnosed disease is viewed as the output classification results. To enable such self-learning, the system may include a database that is securely controlled by a WearNet administrator. This will enable WearNet users to share their monitor and diagnosis results thereby improving the automatic diagnosis capability.

III. Human Factors

The success of the presently-disclosed smart health system may be improved by its ability to capture the human factors that affect its design. These include the biocompatibility of the nanoplasmonic biochips and the wearable devices ability to collect, process, and distribute sensitive data related to the users' health.

(a) Implanted Biochip Regeneration

The performance of an implanted biochip may be expected to degrade over time due to factors such as surface biofouling caused by nonspecific binding of biomaterials (biomolecules, cells), or the reduction of binding receptors, etc. The former effect can inhibit the access and binding of a target analyte to sensor receptors, the latter effect leads to a reduction of bound analyte. These effects and others can severely limit the sensor signals, and may need to be addressed to broadly advance applications of imbedded sensors. The presently-disclosed system may utilize minimally invasive methods for addressing such issues, such as, for example, transcutaneous application of sensor regeneration agents, enthalpic and entropic interactions, chemical and electrochemical regeneration, etc. The system may utilize noninvasive methods involving acoustic, thermal, optical, and electromagnetic transduction mechanisms (focused ultrasound (sonication), photothermal heating, optical tweezing, etc.) that can potentially dislodge fouling agents. include to delodge fouling agents.

(b) Biocompatibility and Photothermal Effects Analysis

The in-vivo sensing and networking technologies described herein may result in irradiating tissue with laser light to enable the use of the plasmonic nanoprobes. As such, in order to ensure biocompatibility and avoid tissue damage, it may be important understand and control fundamental light-matter interactions from the cellular to the tissue level, i.e., to limit the laser-induced heating of tissue to tolerable levels. Tissue heating involves many thermodynamic processes that act in parallel, over different temperature ranges and with different reaction rates. These effects include skin burns, collagen denaturation (breakdown) and cellular necrosis (destruction), among others. The local laser beam fluence rate laser $\Phi$ (W/m$^2$) may be controlled to avoid deleterious tissue heating and damage. To this end, computational modeling may be used to predict the laser-induced temperature rise in tissue from first principles using Penne's bioheat equation, which takes into account blood flow, $$\rho C_T \left(1 + \tau \frac{\partial T}{\partial t}\right)$$

$$\frac{\partial T}{\partial t} = k \nabla^2 T - \omega_b C_b \rho_b (T - T_b) + \left(1 + \tau \frac{\partial}{\partial}\right)((\mu_{tissue} + \sigma_{BC})\Phi_{laser} + Q_{ket}).$$

In this equation T is the local tissue temperature (K), $\rho$ is the tissue density (kg/m$^3$), $C_T$ is the heat capacity of tissue (J kg$^{-1}$ K$^{-1}$), k is the diffusion due to blood flow (W/mK), $C_b$ is the heat capacity of blood, $\omega_b$ is the perfusion due to blood flow (kg$_b$/kg$_{tissues}$), $\rho_b$ is the density of blood, $T_B$ is the arterial blood temperature and $\tau$ is the relaxation time. The nanoplasmonic biochip contributes to the local tissue heating through the per absorption cross-section $\sigma_{BC}$ (m$^2$). $\sigma_{BC}\phi_{laser}$ is the laser-induced heat generated per unit volume by the biochip (W/m$^3$), which will be maximum at their localized LSPR. The other heat generation terms are $Q_{tissue}=\mu_{tissue}\phi_{laser}$, where $\mu_{tissue}$ is the indigenous optical absorption coefficient of the tissue ($m^{-1}$) and $Q_{met}$ is the metabolic heat (W/m$^3$) generated within tissue, which is typically negligible compared to the laser heating. Equation (1) may be solved to predict the temperature rise in target tissues from first principles to enhance embodiments of the networking system and biochips. Viable levels of laser fluence $\phi_{laser}$ and biochip properties ($n_p$ and $\sigma_{BC}$) may be used to limit heating.

(c) Privacy and Confidentiality

Besides the user privacy protection during the data sharing and system self-learning discussed in Section II.b, data security may be implemented throughout the entire data transmission procedure. As shown in FIG. 7, there may be two steps in the data transmission of embodiments of the WearNet system: a wireless Bluetooth link between the wearable interface device and remote processor (e.g., smartphone), and the wireless/wired link between the remote processor and a data server or a remote medical doctor. The security of the link between the remote processor and the remote server or doctor can be provided by the security protocols used in the cellular network, including (1) authenticating users by the international mobile subscriber identity (IMSI, kept in the SIM card) and a shared secret key; and (2) encrypting user data through various encryption, confidentiality, and integrity algorithm sets. The security of the wireless Bluetooth link may be achieved using, for example, pre-shared key authentication and encryption algorithms.

For the WearNet system, while the state-of-the-art security solutions for cellular networks are sufficiently strong, there exist potential security risks for the Bluetooth link. Due to the energy constraints and computation limitations of the nanosensors and the wearable devices, the length and randomness of the passkey and link key for the Bluetooth pairing and communication cannot be arbitrarily long/strong, which enables two types of attacks: (1) an eavesdropping attack that can leak user's raw measurements to an adversary; and (2) a man-in-the-middle attack that allows an adversary to send corrupted measurement data to the smartphone. To address those potential security risks, other energy-efficient and low-complexity security protocols may be used for the Bluetooth link between the wearable device and the smartphone. For example, a friendly jamming device may be used where either the wearable device or the smartphone radiate a strong noise signal during the wireless data transmission. On the one hand, the eavesdropper cannot detect the transmitted data, which disabled their attacks. On the other hand, the smartphone can extract the data from the noise since the smartphone knows all the parameters of the self-generated noise. Other security protocols may be used in addition to, or instead of, those described herein.

IV. System Integration and Testbed Development (a) Integration of the Wearable Device Some embodiments of the wearable interface device comprise of two main elements: a nanosensing front-end (laser sources and CCD detector) and an integrated controller circuit. Recently, with the rapid development of flexible electronics, integration of electronic circuits on a flexible plastic platform such as polydimethylsiloxsane (PDMS) elastomer has led to flexible skin-attachable sensors. In some embodiments, the nanophotonic devices, including lasers and detectors discussed in previous sections, may be implemented on a polymer-based flexible platform, which can be further integrated on wearable devices.

Figure 9:
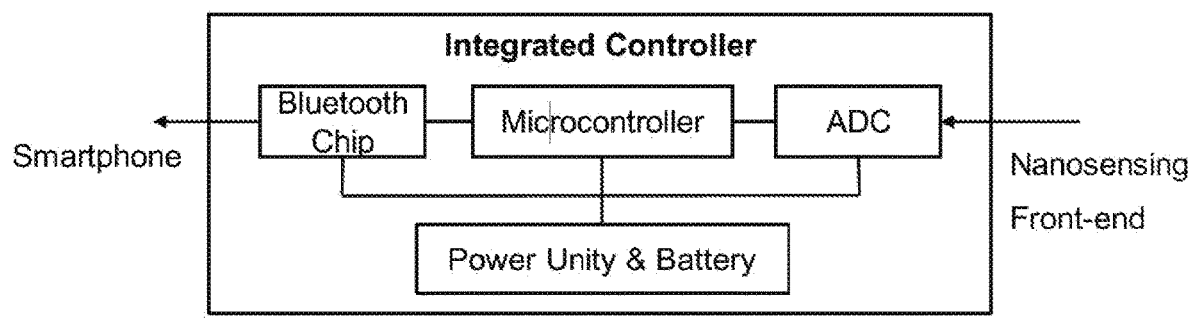
FIG. 9 is a diagram of an exemplary integrated controller circuit design.

Some embodiments of the integrated controller circuit include three major functions: (1) to convert the analog measurements from the CCD array to digital signals; (2) to forward the digitized measurement data to the remote processor through Bluetooth link; and (3) to control the intelligent logic of the wearable device, including, for example, sleep/wake up, Bluetooth pairing, and jamming for security, among others. FIG. 9 illustrates an exemplary design that includes a microcontroller to implement the logic and coordination of the other components, an ADC to convert the analog signal from the detectors (e.g., CCD, etc.) and send the digital data to the microcontroller, a Bluetooth radio chip and 2.4 GHz patch antenna to transmit the digital measurements to the smartphone, and a power unit to supply the power to all the components.

(b) System Testbed

Several testbeds can be used in order to characterize the performance of embodiments of the presently-disclosed system.

Tissue-Equivalent Phantoms (TEPs) TEPs are specially prepared synthetic materials designed to have optical (scattering, absorption) and thermal (heat capacity, diffusivity) properties that match human tissue over a desired frequency range. TEPs can be used to characterize the scattering, absorption, attenuation of EM waves within select tissues due to both the incident laser light and radiation from embodiments of the nanoplasmonic biochips. Photothermal tissue heating can also be characterized using TEPs, and resulting models can be validated.

Figure 10:
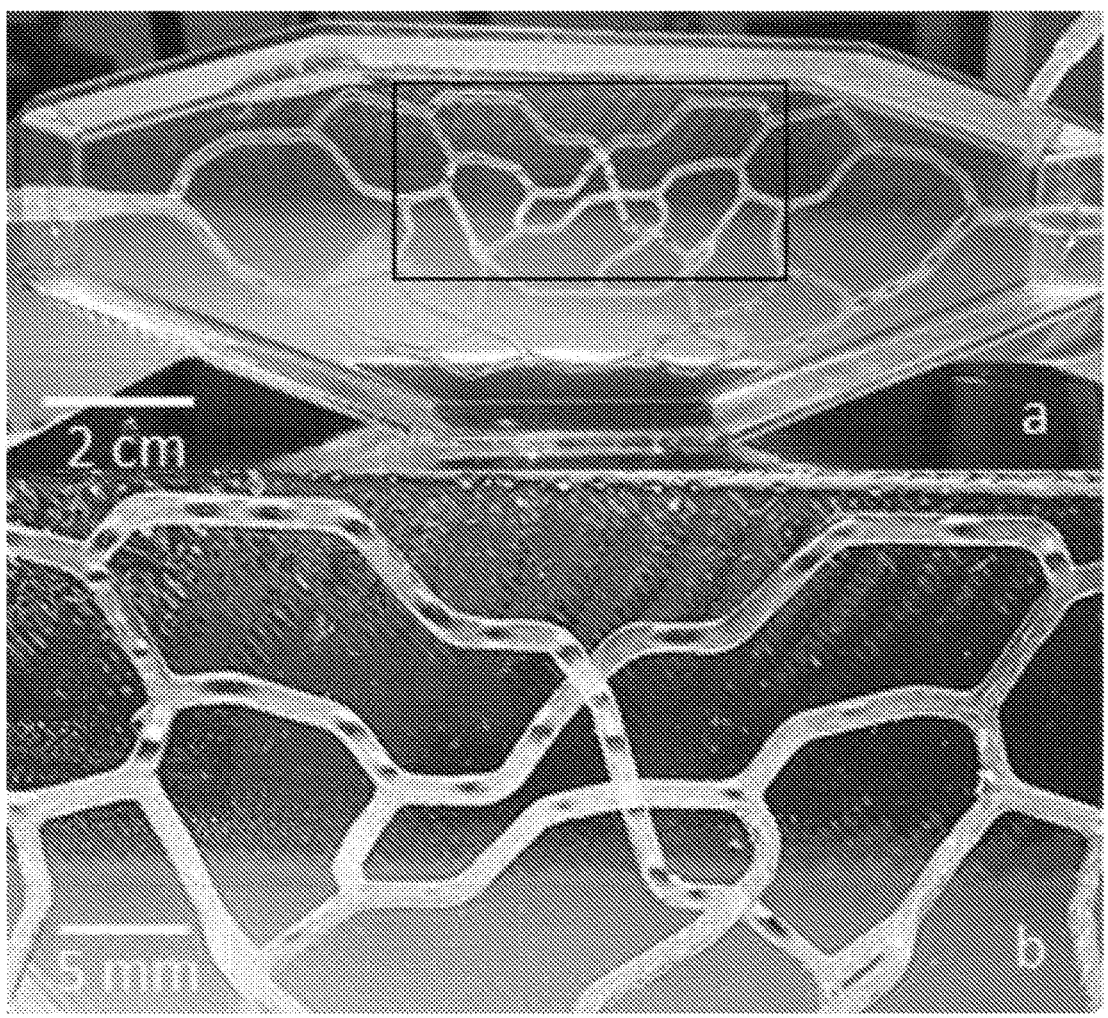
FIG. 10 shows a fabricated microcirculation network: (a) general view and (b) close-up view showing flow.

Microcirculation Tissue-Equivalent Phantoms Microcirculation networks comprise vessels (<100 μm in diameter), arterioles, capillaries and venules. Microcirculation tissue-equivalent phantoms can be fabricated (see FIG. 10). Specifically, microfluidic flow networks can be fabricated within TEP materials to mimic in-vivo blood-flow conditions. Such phantoms can then be used to characterize the irrigation of the implanted biochips within the circulatory system.

WearNet Integrative Testbed A testbed for the disclosed technology can be realized by implanting a nanoplasmonic biochip described herein into a microcirculation tissue-equivalent phantom networks platform (FIG. 10) and utilizing a prototype wearable device, having a nano-sensing front-end (Section I.c) and microcontroller (FIG. 9), to excite and measure the biochip-scattered signal collectively, and send it via Bluetooth to a smartphone. A mobile app that implements the data reconstruction and analysis algorithms (Section II) can be used with the collected data. Performance parameters such as, for example, measurement SNR as a function of the number of active nano-sources and detectors on the wearable device, SNR as a function of the on-off duty cycle of the optical nano-sources, and body temperature increase as a function of the number of active nano-sources and their duty cycle, can be analyzed.

Although the present disclosure has been described with respect to one or more particular embodiments, it will be understood that other embodiments of the present disclosure may be made without departing from the spirit and scope of the present disclosure.

We claim:

1. A system for detecting and measuring biomarkers, comprising:
   an implantable sensor configured to be implanted in an individual, comprising:
   an array of Surface Plasmon Resonance (SPR) biosensors; and
   a plurality of optical couplers located at a top surface of the implantable sensor, each optical coupler operatively configured such that light received at the optical coupler is focused to a corresponding biosensor of the array of SPR biosensors;

an interface device configured to be worn by the individual proximate to the implantable sensor, comprising:

a plurality of emitters, each emitter configured to emit light to a corresponding optical coupler of the implantable sensor; and a plurality of detectors, each detector configured to receive light reflected by a corresponding biosensor of the implantable sensor.

2. The system of claim 1, wherein the array of SPR biosensors comprises:

a substrate with a top surface and a bottom surface, wherein the top surface is configured to be positioned toward the exterior of the user's body when implanted;

a plurality of gratings arranged on the bottom surface of the substrate; and an SPR film on the plurality of gratings.

3. The system of claim 1, wherein the SPR film is a metallic film.

4. The system of claim 1, further comprising a biocompatible gel between the substrate and the plurality of gratings.

5. The system of claim 1, wherein each emitter in the plurality of emitters is a laser.

6. The system of claim 5, wherein each laser in the plurality of emitters is an orbital angular momentum microlaser.

7. The system of claim 5, wherein each laser in the plurality of emitters is a single-mode microring laser.

8. The system of claim 5, wherein each laser in the plurality of emitters is a three-dimensional subwavelength metallo-dielectric semiconductor laser.

9. The system of claim 8, wherein each three-dimensional subwavelength metallo-dielectric semiconductor laser incorporates a dielectric shield layer.

10. The system of claim 1, wherein the interface device further comprises an interface processor, wherein the interface processor post-equalizes a measured signal, filters stochastic and ambient background noise from the measured signal, and combines the measured signal at each nanophotonic detector.

11. The system of claim 1, wherein the interface device further comprises a transceiver.

12. The system of claim 11, wherein the transceiver is a Bluetooth transceiver.

13. The system of claim 1, further comprising a remote processor in wireless communication with the interface device.

14. The system of claim 13, wherein the remote processor is a smartphone.

15. The system of claim 13, wherein the remote processor is configured to transmit the data to a practitioner for analysis.

16. The system of claim 13, wherein the remote processor is configured to process the data into an anonymous data set and store the anonymous data set on a data server.

* * * * *